United States Patent [19]

Harris

[11] Patent Number: 4,813,418

[45] Date of Patent: Mar. 21, 1989

[54] NERVE FIBER STIMULATION USING SYMMETRICAL BIPHASIC WAVEFORM APPLIED THROUGH PLURAL EQUALLY ACTIVE ELECTRODES

[75] Inventor: Frank W. Harris, Boulder, Colo.

[73] Assignee: Staodynamics, Inc., Longmont, Colo.

[21] Appl. No.: 9,760

[22] Filed: Feb. 2, 1987

[51] Int. Cl.$^4$ ............................................. A61N 1/36
[52] U.S. Cl. .................................................. 128/421
[58] Field of Search .................. 128/419 PG, 421–423

[56] References Cited

U.S. PATENT DOCUMENTS

| | | | |
|---|---|---|---|
| 2,375,575 | 5/1945 | Morland et al. | 128/421 |
| 2,498,882 | 2/1950 | Fizzell et al. | 128/421 |
| 3,522,811 | 8/1970 | Schwartz et al. | 128/419 C |
| 3,946,745 | 3/1976 | Hsiang-Lai et al. | 128/422 |
| 4,147,171 | 4/1979 | Greene et al. | 128/419 R |
| 4,237,899 | 12/1980 | Hagfors et al. | 128/422 |
| 4,256,116 | 3/1981 | Meretsky et al. | 128/419 R |
| 4,324,253 | 4/1982 | Greene et al. | 128/421 |
| 4,640,286 | 2/1987 | Thomson | 128/421 |

Primary Examiner—Ruth S. Smith
Attorney, Agent, or Firm—Robert E. Harris

[57] ABSTRACT

Nerve fiber stimulation is disclosed using a symmetrical biphasic waveform applied through plural active electrodes to increase the activity of the nerve fibers then selected for stimulation. Bi-phased pulse pairs are repeatedly symmetrically generated and applied to the nerve fibers to be stimulated with the first pulse of each pulse pair being a positive polarity pulse applied through a first electrode to cause the nerve fibers to be set into the refractory period and with the second pulse of each pulse pair being a negative polarity pulse applied through the first electrode to occur substantially at the end of the refractory period for the nerve fibers then to be stimulated to thereby excite those nerve fibers. The pulse pairs are also applied in inverted polarity through a second electrode with the inverted second pulse thus resulting in an applied positive pulse at the second electrode to cause the nerve fibers to be stimulated to be set into the refractory period and with the inverted first pulse of the succeeding pulse pair resulting in an applied negative pulse at the second electrode occurring substantially at the end of the refractory period for the particular nerve fibers to be stimulated to thereby excite those nerve fibers. Plural channels having dual active electrodes can be provided with applied bi-phased pulses being timewise offset from one another to maintain isolation between channels.

18 Claims, 3 Drawing Sheets

+ LEADING EDGE TRIGGER
− TRAILING EDGE TRIGGER

NERVE FIBER STIMULATION USING SYMMETRICAL BIPHASIC WAVEFORM APPLIED THROUGH PLURAL EQUALLY ACTIVE ELECTRODES

FIELD OF THE INVENTION

This invention relates to electrical nerve fiber stimulation, and, more particularly, relates to nerve fiber stimulation using a symmetrical biphasic waveform applied through plural active electrodes.

BACKGROUND OF THE INVENTION

It has heretofore been common to electrically stimulate nerves for various therapeutic purposes, and medical practitioners have heretofore used electrical stimulation for stimulating muscle activity, relieving pain, and producing sensation, among other therapeutic purposes.

The sequence of effects produced by electrical stimulation, as its intensity is increased, is known to generally follow a pattern of a perception of an electrical sensation (usually tingling), an increase in sensation, fasciculation muscle contraction, pain, and then injury in the form of electrical burns or cardiac arrhythmias.

While therapeutic effects often occur while stimulation is applied with a continuous intensity below that necessary to produce muscle contraction, it should be remembered that exceptions do occur to the general effect pattern such as, for example, when a steady DC current is applied and slowly increased in intensity, muscle contraction cannot be obtained, though the other effects occur in the same order.

Electrical stimulation has been attempted and/or realized through use of a wide variety of electrical waveforms and these waveforms have ranged from a purely DC (galvanic) current or voltage to many different combinations of electrical pulses of various shapes and durations. While at least some such waveforms have provided some degree of desirable effect, the results achieved have been random with no clear understanding of how optimization might, or could, be achieved.

As mentioned above, stimulation has been made to occur with many different types of pulses, and pulse pairs that include both positive and negative pulses have heretofore been suggested (see, for example, U.S. Pat. Nos. 2,375,575, 3,946,745, 4,237,899, and 4,256,116).

While these patents suggest that bi-phased pulse pairs can be utilized for therapeutic purposes, there is no apparent teaching in these patents of devices or methods that are shown to optimize stimulation or enhance stimulation using a symmetrical waveform in conjunction with dual active electrodes. Optimization is important to achieve results with minimum power and maximum effect on functions of the body controlled by the fibers specifically stimulated, and apparatus and method for optimization of stimulation is shown and claimed in U.S. patent application Ser. No. 667,873, entitled "Optimized Nerve Fiber Stimulation", filed Nov. 2, 1984 by Thomas H. Thomson, issued as U.S. Pat. No. 4,640,286 on Feb. 3, 1987, and owned by the Assignee of this invention. This U.S. patent application Ser. No. 009,927 entitled "Nerve Fiber Stimulation Using Plural Equally Active Electrodes", filed Feb. 2, 1987, by Thomas H. Thomson, is a continuation-in-part of U.S. patent application Ser. No. 667,873 (now U.S. Pat. No. 4,640,286), and is owned by the Assignee of this invention. U.S. patent application Ser. No. 009,927 is directed to use of dual active electrodes using bi-phasic waveforms, and this invention utilizes a symmetrical biphasic waveform to stimulate plural active electrodes.

SUMMARY OF THE INVENTION

This invention provides apparatus and method for nerve fiber stimulation using plural active electrodes having a symmetrical biphasic waveform coupled thereto to enhance nerve fiber stimulation to thereby increase the overall activity of the nerve fibers then being stimulated.

Symmetrical biphasic pulse pairs are utilized with each of the pulses of each pair being separated by a distance, in time, comparable to the retractory period for the particular nerve fibers then being stimulated and with the spacing between the last pulse of each pair and the first pulse of the next occurring pulse pair being also spaced from one another a distance, in time, comparable to the refractory period for the particular nerve fibers then being stimulated. By repeated application of the pulse pairs to each of a plurality of electrodes with a spacing therebetween based upon the refractory period for the nerve fibers to be stimulated, a positive pulse is applied to a first electrode while a negative pulse is later applied to the first electrode, and an inverted pulse of negative polarity is applied to a second electrode (as a pulse of poitive polarity) while an inverted pulse of negative polarity is later applied to the second electrode (as a pulse of negative polarity) so that both electrodes are made substantially equally active to enhance nerve fiber stimulation.

It is therefore an object of this invention to provide improved apparatus and method for stimulating nerve fibers.

It is another object of this invention to provide improved apparatus and method for stimulation of nerve fibers through plural active electrodes.

It is another object of this invention to provide improved apparatus and method for enhancing stimulation of nerve fibers using a symmetrical biphasic waveform applied through plural active electrodes.

It is still another object of this invention to provide improved apparatus and method for enhancing stimulation of nerve fibers using a symmetrical biphasic waveform applied at preselected different times to different channels each of which includes dual active electrodes.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
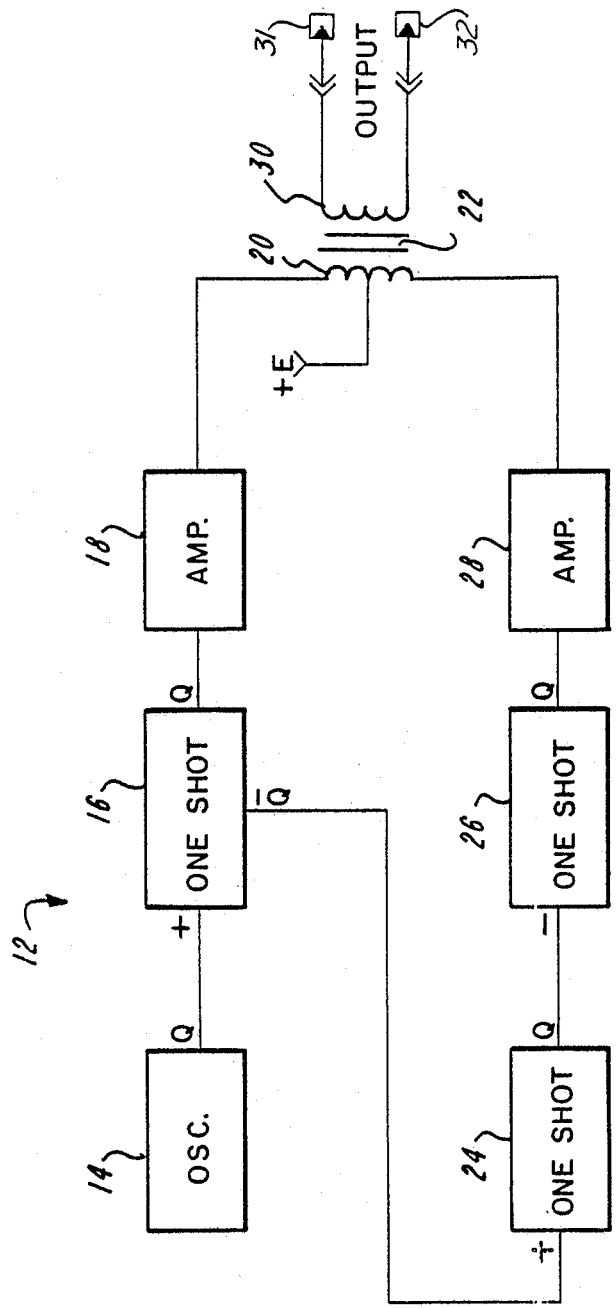
FIG. 1 is a block and schematic diagram illustrating apparatus active at one working electrode for enhancing electrical stimultion of nerve fibers.

To understand enhancement of stimulation according to this invention, the nature and function of nerve fibers should first be understood. Individual nerve cells are called neurons and are contained in cable-like bundles in the nervous tissue called nerves. The individual nerve fibers comprise a portion of a nerve cell extending from the nerve cell body to its end point where the activity for which that neuron is responsible is either detected by the neuron or influenced by the neuron. In peripheral nerves (i.e., those not contained in the spine or skull or in the autonomic nervous system), nerve fibers extend from the spinal cord as a continuous filament to the point where they interact with other tissue.

Nerve fibers conduct information in much the same manner as does a cable, and generally carry information in binary form. The number of nerve pulses per unit time determines the degree of activity since each nerve pulse for a given nerve fiber is identical (for practical purposes) to every other pulse relayed by that fiber.

The electrical activity of nerve fibers can be generalized, for purposes as set forth herein, and terminology considered important to understanding the invention are as follows:

Action Potential is the firing of the neuron caused by either natural or artificial stimulation of the nerve;

Absolute Refractory Period is a period of time when the nerve cannot be caused to fire (i.e., to produce a second pulse), regardless of how strongly it is stimulated, and this period of time sets the upper limit on the frequency or the rate that the neuron can fire; and Relative Refractory Period is a period of time wherein a stronger than normal stimulus is required to fire, or excite, the nerve, with the strength or intensity of the stimulus required to stimulate the nerve fiber diminishing over time until it reaches a minimum when the fiber has reached its resting potential, and the relative refractory period can contribute to setting the upper limit of the expectation (firing) rate of the neuron, depending upon stimulus intensity.

Neurons may be classified by their fiber diameters and the activity for which they are responsible. When so classified, six basic groups are preferably formed (other groupings are occasionally used, but this grouping is convenient for understanding the invention). The time length which the neuron remains within the various periods mentioned are different for each class of neurons. The fiber class, specific function, size diameter, conduction velocity (CV), refractory period time (RP), and peak hyperexcitability time (HE) for five groups are set forth in Table I as follows:

TABLE I

| | NERVE FIBER CHARACTERISTICS | | | | |
|---|---|---|---|---|---|
| | FIBER CLASS | | | | |
| | A alpha | A beta | | A gamma | C |
| Function | MOTOR FAST TWITCH | MOTOR MEDIUM TWITCH | SENSORY | MOTOR SLOW TWITCH | PAIN & AUTONOMIC |
| SIZE DIA. (MICROMETERS) | 17 | 15 | 13 | 8 | <1.3 |
| CV M/SEC | 80–90 | 60–70 | 50–60 | 10–40 | .7–2.3 |
| RP | .12 MSEC | .5 MSEC | .6 MSEC | 1.1 MSEC | 1.8 MSEC |
| HE | 2 MSEC | 2.5 MSEC | 2.5 MSEC | 4 MSEC | 4.5 MSEC |

Nerves contain a mixture of the above-listed fibers with large numbers of each type of fiber being normaly included in the nerve. The effect of electrical stimulation is increased by increasing the frequency with which the stimulus is able to fire the individual fibers (as noted previously) as well as increasing the total number of individual fibers of the same class which are excited simultaneously.

For a more complete explanation of the foregoing, the following references can be utilized: Roger Warwick and Peter L. Williams, GRAY'S ANATOMY, 35th British Edition (Philadelphia: W.B. Saunders Company), multiple citations; Verrnon B. Mountcastle, MEDICAL PHYSIOLOGY, 14th ed. (St. Louis, Toronto, London: The C.V. Mosby Company), vol 1 and 2, multiple citations; and Percival P. Newman, NEUROPHYSIOLOGY, (New York: SP Medical & Scientific Books) multiple citations.

An apparatus useful for producing a bi-phased pulse pair, active at one working electrode, is shown by the generalized block diagram of FIG. 1.

As shown in FIG. 1, apparatus 12 includes oscillator 14 that provides an input signal to one shot multivibrator 16 to trigger the multivibrator at a leading edge of the input signal from oscillator 14. The Q output from one shot multivibrator 16 is coupled through amplifier 18 to one side of primary winding 20 of transformer 22, while the $\overline{Q}$ output from one shot multivibrator 16 is coupled as an input to one shot multivibrator 24 with a leading edge of this input signal triggering multivibrator 24.

The Q output from one shot multivibrator 24 is coupled to one shot multivibrator 26 with a trailing edge of this input signal triggering multivibrator 26. The output from one shot multivibrator 26 is coupled through amplifier 28 to the other side of primary winding 20 of transformer 22.

The output taken from secondary winding 30 of transformer 22 is a series of pulse pairs which are coupled to electrodes 31 and 32 for noninvasive application of the pulse pairs to the nerve fibers then selected for stimulation. The pulse pairs produced at the output (from secondary winding 30 as shown in FIG. 1) are spaced, in time, by a distance equal to that of the refractory period in order to enhance performance.

This invention utilizes the foregoing to enhance the therapeutic benefit of electrical stimulation. For simplicity of explanation, the invention is described hereinafter with respect to application to a particular type of nerve fibers (pain neurons) to achieve pain reduction, and is to be considered as an example of the overall invention. Each of the other types of neurons is susceptible to the same factors (as set forth hereinafter) except that the time periods are different (but still specific) for each class of neurons.

The important factors and their apparent result for pain reduction are as follows:

(1) A positive pulse applied through a first electrode to the nerve fibers sets the nerve fibers into a condition similar to the refractory period (this pulse is important because it apparently causes a large number of nerve fibers to be synchronized at the same time into the same state or period, thereby causing them to return to the hyperexcitability condition simultaneously);

(2) A negative pulse thereafter applied through the first electrode to the nerve preferably 1.8 milliseconds (ms) later (range of about 1.7 ms to about 2.0 ms) excites the nerve fibers (a negative pulse has been found to provide better stimulation of the action potential, and the negative pulse is timed to arrive just as the nerve fibers leave the refractory period so that the time interval between the pulses of the pulse pair is therefore the same as the time interval of the retractory period—if applied apparently earlier or later, fewer nerve fibers are excited because they are either in the relative refractory period, or beyond, and, therefore, are harder to excite);

(3) Inverting of the negative pulse to a positive pulse and applying the resulting positive pulse through the second electrode (i.e., the second electrode receives the mirror image of the waveform applied to the first electrode) to the nerve fibers results in a pulse suitable to set the nerve fibers in the same manner as above described for the positive pulse applied through the first electrode;

(4) Inverting of the positive pulse of the next occurring pulse pair and applying the resulting negative pulse to the nerve fiber results in a pulse suitable to excite the nerve fibers in the same manner as described above for the negative pulse applied through the first electrode since this pulse occurs 1.8 ms (range of about 1.7 ms to 2.0 ms) after the preceding applied positive pulse through the second electrode;

(5) Application of the next occurring positive pulse, applied to the nerve fibers after a time period following application of bi-phased pulses of positive are then negative polarity, which time period is based upon the time of peak relative excitability (i.e. a time period equal to the known time between the action potential and the maximum hyperexcitability condition of the nerve fibers to be stimulated, again sets the nerve fibers; and (6) The width of the pulses is maximized at about 60 microseconds (range of about 50 microseconds to about 70 microseconds) with the pulse shape or waveform (for example, rise time and or fall time) being not as important, and pulse amplitude and duration being preferably the same for both the positive and negative pulses of each pulse pair.

Figure 2:
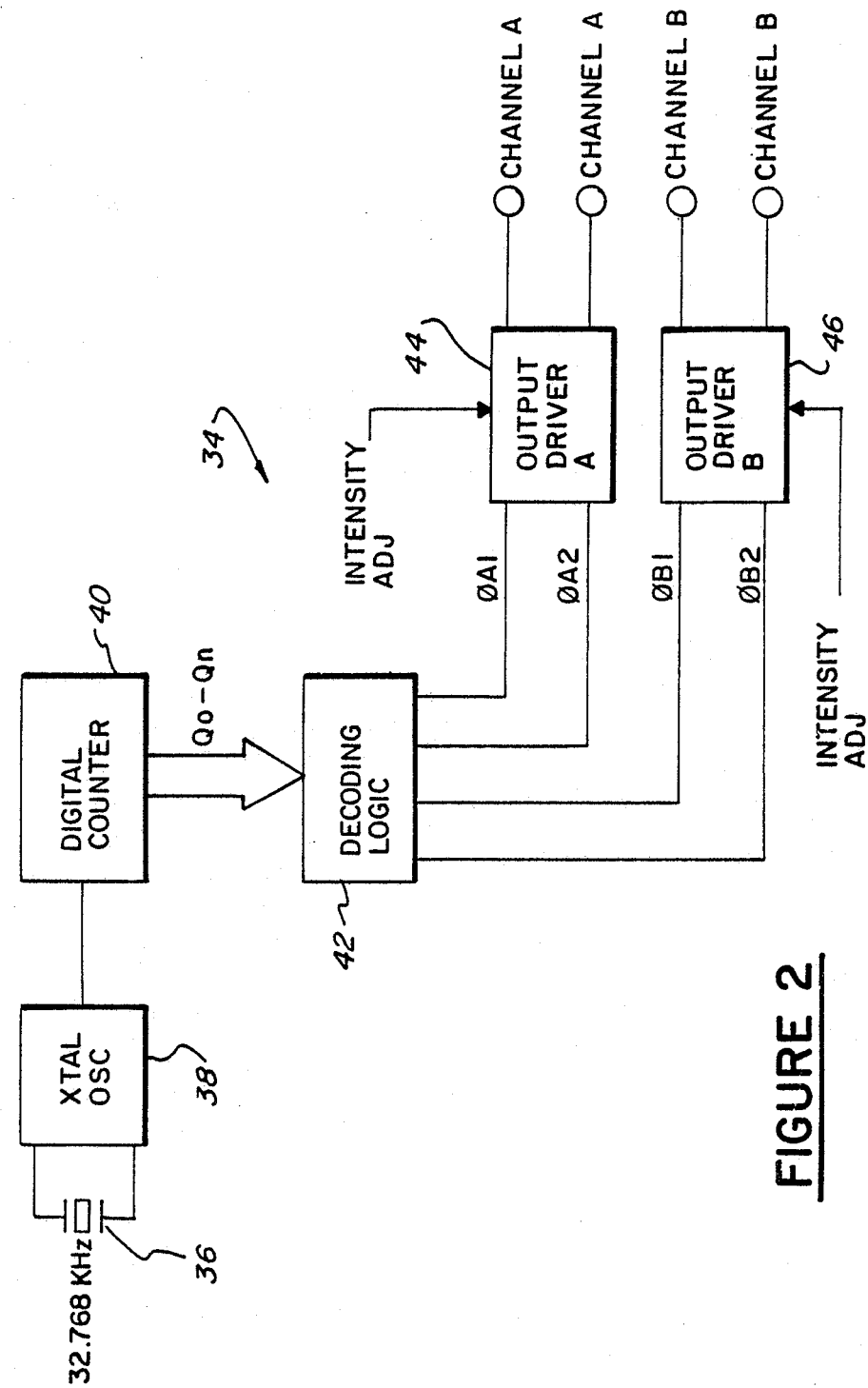
FIG. 2 is a block diagram of apparatus providing a symmetrical biphasic waveform applied through plural active electrodes according to this invention.
Figure 3:
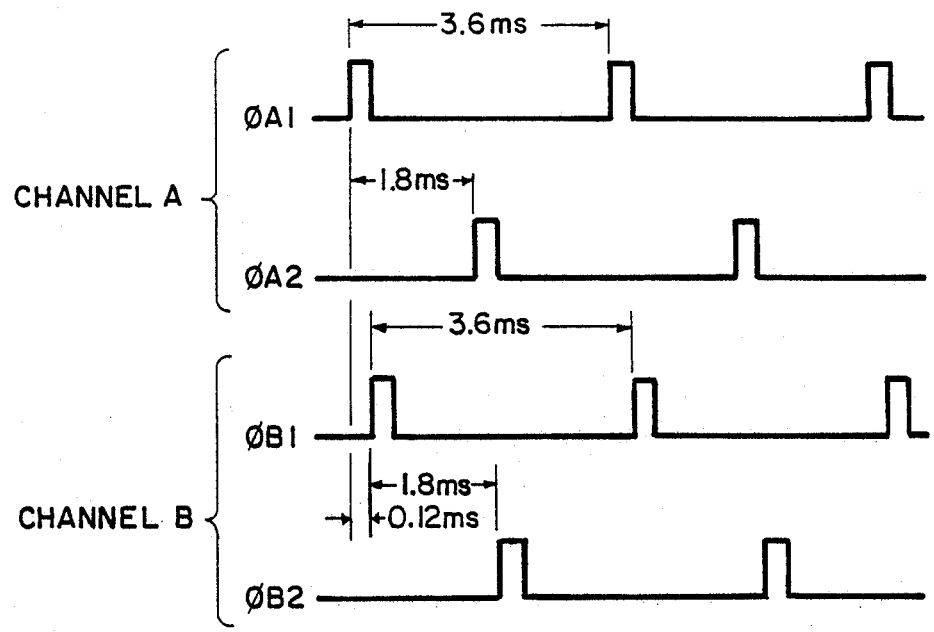
FIG. 3 is a typical representation of phased pulse outputs useful for generating the biphasic waveform of this invention.

A now preferred digital embodiment 34 of apparatus for this invention is shown in FIG. 2. As shown, crystal 36 is utilized as a part of crystal oscillator 38 to provide output clock pulses. These pulses are coupled through digital counter 40 which produces a plurality of outputs, as desired, which are coupled through decoding logic unit 42 (which could also be a ROM unit) to provide a plurality of identical waveforms each of which includes timewise spaced pulses with the corresponding pulses of each waveform being offset with respect to one another, as indicated in FIG. 3.

As indicated in FIG. 2, outputs φA1 and φA2 are applied to output driver 44 for a first channel (channel A), while outputs φB1 and φB2 are applied to output driver 46 for a second channel (channel B). It is to be realized, however, that a single channel could be utilized, if desired.

At output driver 44, the pulses of output φA2 are inverted with respect to those of output φA1 (as can be achieved by connecting the output to opposite sides of a transformer is indicated in FIG. 1 or, as is preferred, connecting the φA2 output through an inverting amplifier) so that the output coupled from output driver 44 includes biphased pulses as indicated in FIG. 4A.

While not specifically illustrated, it is to be realized that while one electrode connected to output driver 44 (an electrode connected to the positive output for Channel A, for example) receives pulses as illustrated in FIG. 4A, the other electrode connected to output driver 44 (an electrode connected to the negative output for Channel A, for example) will receive an inverted polarity, or mirror image, of the waveform received at the other electrode (i.e., when the electrode connected to the positive output receives a positive pulse the electrode connected to the negative output receives a negative pulse and when the electrode connected to the positive output receives a negative pulse the electrode connected to the positive output receives a positive pulse).

Figure 4:
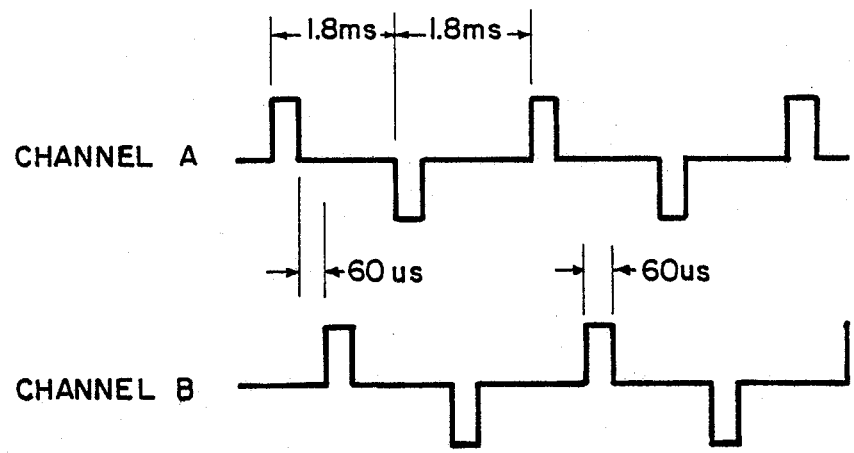
FIG. 4 is a typical representation of the biphasic waveform of this invention shown provided timewise spaced to different application channels.

In like manner, the pulses of output φB2 are inverted with respect to those of output φB1 so that the output from output driver 46 includes bi-phased pulses (as indicated in FIG. 4B), with the pulses applied to the separate electrodes (connected with different ones of the positive and negative outputs) are inverted in polarity with respect to one another in the same manner as described above with respect to the channel A outputs. In addition, as indicated in FIG. 4, the pulses at channel B are preferably timewise offset with respect to the comparable pulses at channel A, as is necessary to achieve isolation between channels when using capacitive coupling (as opposed to transformer coupling which requires no such offset).

As indicated in FIGS. 3 and 4, the pulses are illustrated spaced 1.8 ms from one another. This spacing, as brought out above, has been found to be preferable for pain reduction (as is the object, for example, when using conventional transcutaneous nerve stimulating devices).

Thus, by applying a positive pulse to a first electrode and then applying a negative pulse to the first electrode at a later time corresponding to the known refractory time for the nerve fibers to be stimulated (i.e., 1.8 ms for pain reduction), and inverting the negative pulse to a positive pulse which is applied through a second electrode and then inverting a later occurring positive pulse to a negative pulse which is also applied through the second electrode at a time corresponding to the known refractory time for the nerve fibers to be stimulated (i.e., 1.8 ms for pain reduction), stimulation of the nerve fibers is enhanced since both electrodes are thus made active and the time of application is within the excitability period (i.e., occurs at a time less than the timewise occurrence of the enhanced excitability condition of the nerve fibers to be stimulated). As can be appreciated, this enables use of a symmetrical waveform in which all pulses are timewise equally spaced from one another.

In operation, enhancement of stimulation using a symmetrical waveform applied through dual active electrodes has been found to be useful in connection with human subjects.

A study was made of a plurality of patients, which study included testing with a device using the symmetrical waveform of this invention and with conventional transcutaneous nerve stimulating devices. With respect to 57 patients studied, 46% (26 patients) were found to prefer a device utilizing a waveform in accordance with this invention, 21% (12 patients) preferred the conventional waveform now utilized in TENS devices, 19% (11 patients) expressed no preference, and 14% (8 patients) had a poor response to TENS devices.

With respect to the 57 patients studied, the data collected was incomplete for 12 patients. Table II summarizes the percent of pain relief data obtained with respect to these patients as follows:

TABLE II

| | PERCENT PAIN RELIEF | | |
|---|---|---|---|
| Pt. # | I.W.F. % | C.W.F. % | Difference % |
| Invention Waveform Preferring Patients | | | |
| 7 | 52 | −1 | +53 |
| 9 | 15 | 13 | +2 |
| 10 | 54 | 65 | −11 |
| 11 | 22 | 39 | −17 |
| 14 | 2 | 11 | −9 |
| 20 | 91 | 91 | 0 |
| 21 | 74 | 42 | +32 |
| 28 | 60 | 52 | +8 |
| 29 | 55 | 7 | +48 |
| 32 | 60 | 50 | +10 |
| 33 | 74 | 78 | −4 |
| 34 | 9 | 41 | −32 |
| 38 | 41 | 34 | +7 |
| 39 | 55 | 43 | +12 |
| 42 | 77 | 78 | −1 |
| 44 | 76 | 30 | +46 |
| 45 | 49 | 17 | +32 |
| 46 | 25 | 18 | +7 |
| 51 | 41 | 22 | +19 |
| 54 | 42 | 25 | +17 |
| 60 | 58 | 25 | +33 |
| 47 | 98 | 99 | −1 |
| 48 | 99 | 92 | +8 |
| Conventional Waveform Preferring Patients | | | |
| 4 | 75 | 71 | +4 |
| 5 | 46 | 65 | −19 |
| 13 | 80 | 73 | +7 |
| 15 | 75 | 71 | +4 |
| 19 | 52 | 24 | +28 |
| 24 | 18 | 14 | +4 |
| 25 | 54 | 68 | −14 |
| 30 | 7 | 28 | −21 |
| 31 | 35 | 53 | −18 |
| 35 | 50 | 51 | −1 |
| 43 | 10 | 16 | −6 |
| 58 | 20 | 29 | −9 |
| No Preference Patients | | | |
| 12 | 79 | 84 | −5 |
| 26 | 40 | 30 | +10 |
| 37 | 36 | 58 | −22 |
| 53 | 47 | 35 | +12 |
| 55 | 51 | 45 | +6 |
| 56 | 34 | 59 | −25 |

TABLE II-continued

| | PERCENT PAIN RELIEF | | |
|---|---|---|---|
| Pt. # | I.W.F. % | C.W.F. % | Difference % |
| 57 | 9 | 8.5 | +.5 |
| 59 | 25 | 36 | −11 |
| 66 | 33 | 20 | +13 |
| 52 | 49 | 47 | +2 |

Table II summarizes the hours of pain relief data gathered during patient interviews with respect to 34 patients as follows:

TABLE III

| | HOURS PAIN RELIEF | | |
|---|---|---|---|
| Pt. # | I.W.F. % | C.W.F. % | Difference % |
| Invention Waveform Preferring Patients | | | |
| 47 | 6 | 4.9 | +1.1 |
| 48 | 8.2 | 4.5 | +3.7 |
| 46 | .71 | .57 | +.14 |
| 44 | .67 | 0 | +.67 |
| 42 | 6 | 1.3 | +4.7 |
| 39 | 12 | 4 | +8 |
| 38 | 1.3 | .58 | +.72 |
| 34 | 1.9 | 1.63 | +.27 |
| 33 | .57 | 0 | +.57 |
| 32 | .1 | 0 | +.1 |
| 29 | 3.5 | 0 | +3.5 |
| 28 | 2.1 | 1.5 | +.6 |
| 22 | 1.75 | .29 | +1.46 |
| 21 | 4 | 2.5 | +1.5 |
| 14 | 2 | .32 | +1.68 |
| 11 | 1.5 | .8 | +.7 |
| 10 | 4.25 | 4.5 | −.25 |
| 9 | 2.5 | 1.9 | +.6 |
| 7 | 3.3 | 0 | +3.3 |
| Conventional Waveform Preferring Patients | | | |
| 43 | .63 | .63 | 0 |
| 35 | 3 | 3.5 | −.5 |
| 31 | 0 | 0 | 0 |
| 30 | 1.8 | 3.8 | −2 |
| 25 | .83 | 0 | +.83 |
| 24 | 0 | .12 | −.12 |
| 19 | 2.8 | 2.13 | +.67 |
| 15 | 5 | 4 | +1 |
| 13 | 1.5 | 1.25 | +.25 |
| 5 | 2 | 1.5 | +.5 |
| 4 | 3 | 2.5 | +.5 |
| No Preference Patients | | | |
| 37 | 1 | 3 | −2 |
| 26 | .5 | 0 | +.5 |
| 12 | 1.75 | 2.5 | −.75 |
| 11 | 1.5 | .8 | +.7 |

Table IV summarizes data from patients having a poor response to utilization of transcutaneous nerve stimulatin devices as follows:

TABLE IV

| | POOR RESPONSE PATIENTS | | | | | | |
|---|---|---|---|---|---|---|---|
| | Avg. Pain Scale | Average % Pain Relief | | | Average Hours of Pain Relief | | |
| Pt. # | Before | I.W.F. | S.W.F. | Difference | I.W.F. | S.W.F. | Diff. |
| 1 | 7.8 | 10 | −17 | +27 | 0 | 0 | 0 |
| 2 | 10 | 1 | 2 | −1 | .75 | 2 | −1.25 |
| 3 | 7.0 | −5 | 22 | −27 | .5 | .75 | −.25 |
| 8 | 2.4 | 5 | 28 | −23 | 0 | 0 | 0 |
| 23 | 5.7 | −8 | 4 | −12 | 3 | .33 | +2.67 |
| 50 | 5.3 | 16 | 17 | −1 | | no data | |
| MEANS | 6.4 | 3.2 | 9.3 | −6.1 | .85 | .62 | +.23 |

From this study, it is shown that pain relief using apparatus with the waveform of this invention was enhanced with such relief extending over a longer period than has heretofore been possible using conventional transcutaneous nerve stimulating devices.

As can be appreciated from the foregoing, this invention is thus felt to provide improved apparatus and method for enhancing electrical stimulation of nerve fibers of the human body using a symmetrical biphasic waveform applied through plural active electrodes.

What is claimed is:

1. A device for providing electrical stimulation through plural active electrodes to preselected nerve fibers having known refractory periods and enhanced excitability conditions that occur during known periods following the occurrence of an action potential, said device comprising:

generating means for generating a series of output pulse pairs with each said pair having first and second pulses of positive and negative polarity, respectively, and with said first pulse occurring timewise before said second pulse, said pulses of each said pulse pair being spaced from one another a distance, in time, substantially equal to that of the known refractory period of said preselected nerve fibers to be stimulated, and each pulse of each said pulse pair of said series of pulse pairs occurring so as to be timewise spaced from each corresponding pulse of each adjacent pulse pair a distance less than the timewise occurrence of said enhanced excitability condition of said preselected nerve fibers to be stimulated;

first and second electrodes; and coupling means connected with said generating means and said first and second electrodes to apply said series of output pulse pairs to said preselected nerve fibers through said first electrode and to apply said series of output pulse pairs in inverted polarity to said preselected nerve fibers through said second electrode so that said applied positive pulse of each said pulse pair sets said preselected nerve fibers, and so that said later occurring applied negative pulse of each said pulse pair occurs substantially at the end of said refractory period to excite said preselected nerve fibers, whereby said first and second electrodes are both made active to promote stimulation of said preselected nerve fibers and thereby increase the activity thereof.

2. The device of claim 1 wherein said preselected nerve fibers have a maximum hyperexcitability condition, and wherein said generating means includes means to repeatedly provide said series of pulse pairs such that each said corresponding pulse of each pulse pair occurs with a timewise spacing less than but based upon that of the known time between said action potential and said maximum hyperexcitability condition of said preselected nerve fibers.

3. The device of claim 2 wherein said generating means repeatedly generates said first and second pulse with a substantially equal pulse spacing between each said pulse generated whereby a symmetrical bi-phased waveform is provided.

4. The device of claim 1 wherein said generating means includes means providing for stimulation of at least one class of sensory, motor, pain control and autonomic nerve fibers, and wherein said first and second electrodes are made substantially equally active to stimulate said nerve fibers selected for stimulation.

5. The device of claim 1 wherein said generating means includes digital means for causing generation of said series of first and second pulses.

6. The device of claim 5 wherein said digital means includes digital counter means and decoding logic means.

7. The device of claim 6 wherein said decoding logic means generates a plurality of timewise spaced pulses for providing said series of output pulses.

8. The device of claim 7 wherein said first and second electrodes establish a first output channel, wherein said device also includes third and fourth electrodes establishing a second output channel, and wherein said decoding logic means provides timewise spaced pulses for separate application to each of said electrodes.

9. The device of claim 1 wherein said generating means includes means providing for stimulation of pain reduction neurons by causing said spacing between each of said first and second pulses to be between about 1700 and 2000 microseconds.

10. The device of claim 9 wherein said generating means includes means for causing said spacing between said of said first and second pulses to be about 1800 microseconds.

11. A device for providing electrical stimulation through plural active electrodes to preselected nerve fibers having known refractory periods and enhanced excitability conditions that occur following the occurrence of an action potential, said device comprising:

generating means for generating a series of output pulse pairs each having first and second pulses with said first pulse of each said pulse pair being a positive polarity pulse and said second pulse of each said pulse pair being a negative polarity pulse, said first and second pulses of each said pulse pair and each said second pulse and the timewise adjacent first pulse of a succeeding pulse pair being spaced, in time, from one another a distance substantially equal to the known refractory period of said preselected nerve fibers;

first and second electrodes; and coupling means connected with said generating means and said first and second electrodes to receive said pulses from said generating means and to apply said pulses to said preselected nerve fibers through said first electrode and to apply said pulses in inverted polarity to said preselected nerve fibers through said second electrode so that said first pulse of each said pulse pair acts through said first electrode to set said preselected nerve fibers and said second pulse of each said pulse pair acts through said first electrode substantially at the end of said refractory period for said preselected nerve fibers to excite said preselected nerve fibers, and so that said inverted second pulse of each said pulse pair acts through said second electrode to set said preselected nerve fibers and said inverted first pulse of each succeeding pulse pair acts through said second electrode substantially at the end of said refractory period for said preselected nerve fibers to excite said preselected nerve fibers, whereby both said first and second electrodes are substantially equally active to enhance stimulation of said preselected nerve fibers.

12. The device of claim 11 wherein said generating means includes digital means for generating each of said pulses.

13. The device of claim 12 wherein said first and second electrodes establish a first delivery channel, wherein said device includes third and fourth electrodes establishing a second delivery channel, and wherein said generating means provides said pulse pairs to said coupling means such that each pulse is timewise offset with respect to each corresponding pulse so that said pulse pairs coupled to said first and second delivery channels are offset with respect to one another.

14. A method for enhancing electrical stimulation through plural active electrodes of nerve fibers having predetermined refractory periods and enhanced excitability conditions that occur during known periods following the occurrence of an action potential, said method comprising:

generating a first pulse of positive polarity and applying said first pulse through a first electrode to nerve fibers to be electrically stimulated to thereby set said nerve fibers;

generating a second pulse of negative polarity and applying said second pulse through said first electrode to said nerve fibers to be electrically stimulated to cause excitation thereof, with said second pulse being generated at a time subsequent to said first pulse that is substantially equal to that of the refractory period for said nerve fibers then to be stimulated;

repeatedly generating said first and second pulses with each occurrence of each said first pulse being timewise spaced from each adjacent preceding second pulse a distance that is substantially equal to that of the refractory period for said nerve fibers with the spacing between corresponding adjacent ones of said first and second pulses being sufficiently near to the timewise occurrence of said enhanced excitability condition of said preselected nerve fibers to be stimulated to enhance stimulation of said nerve fibers;

inverting said second pulse and applying said resulting positive pulse through said second electrode to said nerve fibers to be stimulated to thereby set said nerve fibers; and inverting said next occurring first pulse and applying said resulting negative pulse through said second electrode to said nerve fibers to be stimulated to cause excitation thereof.

15. The method of claim 14 wherein said nerve fibers then to be stimulated have a maximum hyperexcitability condition, and wherein said first and second pulses are repeatedly generated so that said negative pulses coupled through said first and second electrodes occur sufficiently close to a time substantially corresponding to the known time of occurrence of said maximum hyperexcitability condition of said nerve fibers to thereby excite said nerve fibers.

16. The method of claim 14 wherein said method includes generating said first and second pulses by digital circuitry.

17. The method of claim 16 wherein said first and second pulses are applied to a third electrode timewise after said corresponding pulses are applied to said first electrode, and wherein said inverted first and second pulses are applied to a fourth electrode timewise after said corresponding pulses are applied to said second electrode, with said first and second electrodes providing a first pulse delivery channel and said third and fourth electrodes providing a second pulse delivery channel.

18. The method of claim 16 wherein said pulse pairs acting through said first and second electrodes stimulate one of sensory, motor, pain control, and autonomic fibers.

* * * * *